US00PP08977P

United States Patent [19]

Button

[11] Patent Number: Plant 8,977

[45] Date of Patent: Nov. 8, 1994

[54] AGLAONEMA PLANT NAMED AMELIA

[75] Inventor: Richard J. Button, Miami, Fla.

[73] Assignee: Sunshine Foliage World, Zolfo Springs, Fla.

[21] Appl. No.: 174,697

[22] Filed: Dec. 28, 1993

[51] Int. Cl.[5] ..... A01H 5/00
[52] U.S. Cl. ..... Plt./88.1
[58] Field of Search ..... Plt. 88.1

*Primary Examiner*—James R. Feyrer

*Attorney, Agent, or Firm*—Foley & Lardner

[57] ABSTRACT

An Aglaonema plant named Amelia characterized by its tricolored leaves having dark green background areas, irregularly shaped light green colored areas which follow the lateral veins, and irregular blotches of a third green color between the lateral veins and terminating at the midrib, and by its branched, dense habit, and rapid growth.

1 Drawing Sheet

The present invention comprises a new and distinct cultivar of Aglaonema, botanically known as *Algaonema hybrida*, and referred to by the cultivar name Amelia.

The new cultivar is a product of a planned breeding program carried out by the inventor Richard J. Button in Miami, Fla. The new cultivar is a product of a cross of unknown parentage.

The cultivar was discovered and selected in Miami, Fla. by the inventor from the progeny of the cross. Asexual propagation by division first carried out in Miami by the inventor and later carried out in Zolfo Springs, Fla. was used to increase the number of plants for evaluation and has demonstrated the stability of the characteristics of the new cultivar from generation to generation.

The following observations, measurements and values describe plants growth in Zolfo Springs, Fla. under shadehouse conditions which closely approximate those generally used in horticultural practice.

The following traits have been repeatedly observed to be characteristics which in combination distinguish Amelia from other Aglaonema of the same general type, for example, the commercially well known cultivar Maria.

1. The leaves of Amelia are tricolored, and have considerably more silver markings than Maria.

2. The leaves, petioles, and stems of Amelia are lighter green than those of Maria.

3. Amelia has more branches than Maria.

4. The growth habit of Amelia is more spreading than that of Maria.

5. Plants of Amelia grow to a marketable size from fewer cuttings in approximately 15% less time than Maria.

All color references are to The Royal Horticultural Society color chart. Colors will vary somewhat depending on horitcultural practices such as light level and fertilization rate, among others, without, however any variance in genotype.

The color photographic drawing comprises a top perspective view of Amelia.

The photograph is of a plant of Amelia grown in a 20.3 cm pot approximately 52 weeks after planting a single 4 leaf cutting and grown under appropriate growing conditions. Colors are as accurate as possible with color illustrations of this type.

Origin: Seedling selected from a cross of unknown parentage.

Classification: *Aglaonema hybrida*, cv, Amelia.

Propagation: Asexual propagation either by division or tissue culture.

Plant: When a 4 leaf cutting is grown in a 20.3 cm pot for 52 weeks under appropriate growing conditions, Amelia is approximately 10.5 cm to 12.7 cm in height, measured from the soil surface to the junction of the petioles of the last two (2) unrolled leaves, and approximately 54 cm to 58 cm in width.

(A) *Stem.*—(1) Growth pattern: The stem is erect in growth and approximately 1.6 cm to 1.8 cm in diameter 5 cm above the soil surface. Internode distance is approximately 1.1 cm to 1.7 cm, 3 cm above the soil. (2) Color: The stem color is 139A.

(B) *Petiole.*—The following information is based on the 4th expanded leaf from the apex. (1) Growth Pattern: The petiole has fleshy edges, referred to as wings, extending from the midrib. The wings are approximately 3 mm to 4 mm wide one-half (½) the distance from the petiole base to the wing apex. The wings extend from the base of the petiole to within approximately 1.4 cm to 1.6 cm of the base of the leaf. The apex of the wings is acute. The petiole follows the stem axis but diverges from the axis approximately 2.2 cm from the leaf base, forming a horizontal distance from the edge of the stem to the leaf base of approximately 3.9 cm to 4.7 cm. (2) Dimensions: The petiole is straight from its base to approximately the end of the wing, and often curved from approximately the end of the wing to the base of the leaf. The petiole is approximately 5 mm in diameter one-half the distance between the top of the wing and the base of the leaf. The petiole is approximately 11.5 cm to 13.0 cm in length. (3) Color: The petiole is 137A-B with numerous spots of 139D. The petiole wings are somewhat darker.

(C) *Leaf.*—(1) Growth pattern: The leaf is ovate with an acuminate apex and a cordate base. The margin is entire. The leaf is asymmetric, with the side of the leaf unrolling first having less surface area than the side unrolling last. The leaf is oriented parallel to the stem axis at the time of full unrolling, changing to approximately 45 degrees above perpendicular to the stem axis as more leaves unroll above it. The midrib is straight over two-thirds the length of the leaf, and curved downward near the leaf tip. The leaf blade is flat from the midrib to the margin, and somewhat wavy along the margin. (2) Dimensions: For the pot size and growing time indicated, the largest leaves are approximately 23.3 cm to 27.7 cm long and approximately 7.2 cm to 9.0 cm wide. Average sized leaves are approximately 21.2 cm to 22.4 cm long and approximately 6.7 cm to 8.5 cm wide. The leaf is moderately thick. (3) Midrib: The midrib is thick and prominent, recessed on the adaxial leaf surface and protruding from the abaxial surface. The color of the midrib on the adaxial surface is 147A-B on new leaves, and 147A on mature leaves. The color of the midrib on the abaxial surface is 147C on new leaves, and 147B with spots of 139D on mature leaves. (4) Primary veins: The primary veins are sunken into the upper surface and protrude slightly from the underside. The primary veins are 147A in color. (5) Color and pattern: The leaf is tricolored on the adaxial surface, with the darker green background areas being closest to 137A but somewhat darker. The lightest colored areas (147B-C) are irregularly shaped but follow the lateral veins, with their base terminating at the midrib. There are irregular blotches of a third color (137B-C) which occupy the space between the lateral veins and terminate at the midrib. The abaxial surface of the leaf is 147B-C in color. Lighter irregular blotches of 147D follow and overlay many of the lateral veins. Small spots of 145D may be present along the leaf blade close to the midrib. (6) Axillary breaks: There are approximately 10 to 12 axillary breaks with at least one leaf expanded. Leaves will show true color and pattern by the first leaf. (7) Inflorescence: Typical of Aglaonema and does not have commercial significance.

(D) *Roots.*—Thick white roots with fine laterals.

General observations: Aglaonema Amelia has tricolored leaves variously marked with silver-green on a dark green background. The plant habit is branched, and dense. The plant grows rapidly, attaining a marketable size from fewer cuttings in less time than the closest commercial comparison, Maria. These combined characteristics make Amelia a unique new cultivar.

I claim:

1. A new and distinct cultivar of Aglaonema plant named Amelia, as illustrated and described.

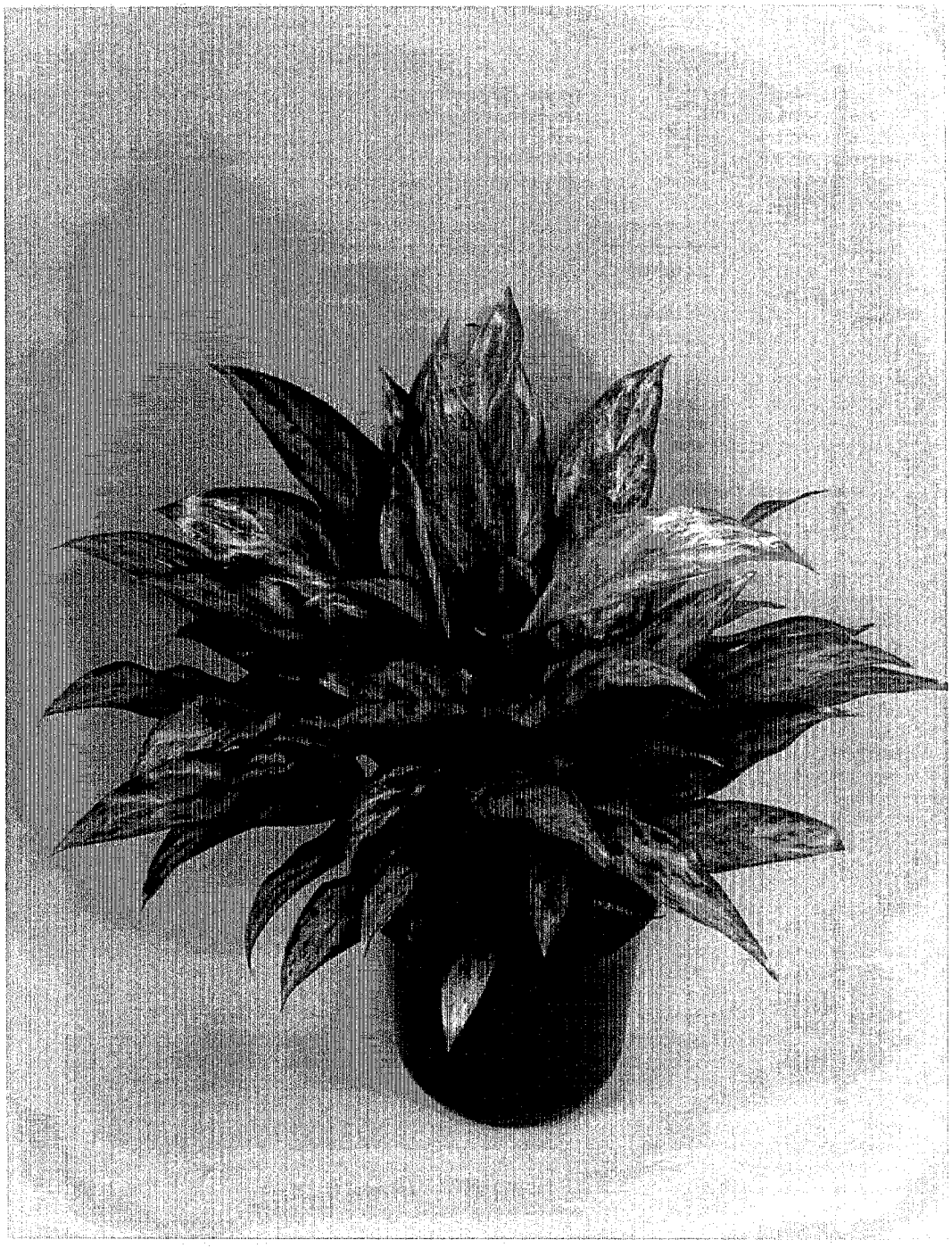

* * * * *